United States Patent [19]

Hirabayashi et al.

[11] Patent Number: 5,143,841
[45] Date of Patent: Sep. 1, 1992

[54] GANGLIOSIDE CERAMIDASE AND PROCESS FOR PRODUCING SAME

[75] Inventors: Yoshio Hirabayashi, Shizuoka; Tatsurokuro Tochikura; Setsu Kadowaki, both of Kyoto; Kenji Yamamoto, Shiga, all of Japan

[73] Assignee: Toyo Jozo Company, Ltd., Shizuoka, Japan

[21] Appl. No.: 553,116

[22] Filed: Sep. 12, 1990

Related U.S. Application Data

[62] Division of Ser. No. 230,465, Aug. 9, 1988, Pat. No. 4,997,760.

[51] Int. Cl.⁵ .......................... C12N 9/78; C12N 9/00
[52] U.S. Cl. .................................... 435/227; 435/183; 435/101; 435/68.1; 435/872; 536/1.1; 536/119; 536/53
[58] Field of Search .............. 435/227, 68.1, 872, 435/183, 101

[56] References Cited

U.S. PATENT DOCUMENTS

3,806,416  4/1974  Mollering et al. ................ 435/183
4,683,198  7/1987  Ishkawa et al. ................... 435/190

OTHER PUBLICATIONS

Conzelmann et al., *Proc. Natl. Acad. Sci. USA.* 75(8), pp. 3979–3983 (Aug., 1978).
Conzelmann et al., *Hoppe–Seyler's A. Physiol. Chem. Bd.* 360, S., pp. 1837–1849 (Dec., 1979).
Li et al., *J. Biol. Chem.*, vol. 256(12), Jun. 25, 1981, pp. 6234–6240.
Burg et al., *Hoppe–Seyler's Z. Physiol. Chem. Bd.* 364, S. pp. 821–829 (Jul., 1983).
Yamamoto et al., *Agric. Biol. Chem.*, vol. 49(3), pp. 611–619 (1985).
Yamamoto et al., *Appl. Environ. Micro.*, vol. 51(5), pp. 1019–1023 (May, 1986).
Sugita et al., *Science*, vol. 178, pp. 1100–1112 (1972).
Sugita et al., *Biochimica et Biophys. Acta*, vol. 598, pp. 125–131 (1975).
Gatt, *J. Biol. Chem.*, vol. 241(16), Aug. 25, 1966, pp. 3724–3730.
Nilsson, *Biochimica et Biophys. Acta*, vol. 176, pp. 339–347 (1969).
Yavin et al., *Biochemistry*, vol. 8, pp. 1692–1698 (1969).
Bannholz et al., *J. Biol. Chem*, vol. 241(16), Aug. 25, 1966, pp. 3731–3737.
Momoi et al., Biochem. J. 205:419–425. 1982.

*Primary Examiner*—Johnnie H. Brown
*Assistant Examiner*—Pamela S. Webber
*Attorney, Agent, or Firm*—Darby & Darby

[57] ABSTRACT

This invention provides a novel ganglioside ceramidase which has a substrate specificity at least for GD1a, GM1, GM2 and GM3 and acts at least on GD1a, GM1, GM2 and GM3 and catalyzes the reaction of hydrolysis of ganglioside to lysoganglioside and fatty acid.

This invention further provides a process for producing the novel ganglioside ceramidase which comprises cultivating ganglioside ceramidase producing strain belonging to the genus Nocardia in a culture medium and collecting ganglioside ceramidase from the culture.

7 Claims, 3 Drawing Sheets

GANGLIOSIDE CERAMIDASE AND PROCESS FOR PRODUCING SAME

This is a division of U.S. patent application Ser. No. 230,465, filed Aug. 9, 1988, which is now U.S. Pat. No. 4,997,760, issued Mar. 5, 1991.

BACKGROUND OF THE INVENTION

This invention relates to a novel ganglioside ceramidase and a process for producing it. More particularly, it relates to a ganglioside ceramidase having physico-chemical properties shown at least by the following substrate specificity and enzyme action.

Substrate specificity; It has substrate specificity at least for GD1a, GM1, GM2 and GM3.

Enzyme action; It acts at least on GD1a, GM1, GM2 and GM3 to catalyzes the reaction of hydrolysis of ganglioside to lysoganglioside and a fatty acid.

Gangliosides are found in cell surface membranes of mammalian tissues and organs and are especially rich in the neural tissues. Gangliosides are sphingolipids produced by the linking of ceramides to oligosaccharides containing at least one acidic saccharide residue, for example, N-acetylneuraminic acid residue. As these gangliosides, for example, GD1a, GM1, GM2 and GM3 have been reported.

This GM2 ganglioside is represented by the structure: GalNAc 1-4(NeuAc 2-3)Gal 1-4Glc 1-1' cer (wherein Gal means galactose, GalNAc means N-acetylgalactosamine, Glc means glucose, NeuAc means N-acetylneuraminic acid and cer means residue of ceramide). GM2 ganglioside accumulates in the lysosomal storage disease, so-called Tay-Sachs disease and is degraded in the lysosome by a series of enzymes, beginning at the non-reducing terminal of the molecule. However, it has been reported that a specific activator is required for catabolism of GM2 ganglioside with β-hexosaminidase A. [Proc. Natl. Acad. Sci. USA. 75, 3979–3983 (1978), Hoppe-Seyler's Z. Physio. Chem. 360, 1837–1849 (1979), J. Biol. Chem. 256, 6234–6240 (1981)]. GM2 ganglioside is not decomposed with exo-β-N-acetyl hexosaminidase isolated from molds such as *Aspergillus niger* [Hoppe-Seyler's Z. Physio. Chem. 364, 821–829 (1983)], *Penicillium oxalicum* [Agric. Biol. Chem. 49, 611–619 (1985)] and *Mucor fragilis* [Applied Environ. Microbiol. 51, 1019–1023 (1986)].

Furthermore, an enzyme which hydrolyzes linkage between sphingosine base and fatty acid of ceramide is called ceramidase; EC 3.5.1.23 [J. Biol. Chem. 241, 3731–3737 (1966), Biochemistry 8, 1692–1698 (1969), Biochim. Biophys. Acta 176, 339–347 (1969), Science 178, 1100–1102 (1972)], but this ceramidase does not hydrolyze the linkage between a sphingosine base and the fatty acid of a glycolipid like ganglioside.

As explained above, exo-N-acetyl hexosaminidase isolated from molds, does not decompose GM2 ganglioside and an enzyme which decomposes GM2 ganglioside has not been known.

The inventors have succeeded in the isolation and purification of an enzyme which produces lysoganglioside GM2 and a fatty acid by hydrolysis of GM2 ganglioside as a substrate from culture of microorganism N285 strain belonging to genus Nocardia collected and isolated from forest soil in Himeji-shi in Hyogo-ken, Japan. This enzyme has been decided to be a novel enzyme having physico-chemical properties and has a novel enzyme action in that it does not utilize Gal-cer, Glc-cer Lac-cer, Gb3-cer and asialoGM1 as substrate, but utilizes at least GD1a, GM1, GM2 and GM3 as substrate and hydrolyzes ceramide in the molecule of this ganglioside into sphingosine base and fatty acid to produce lysoganglioside and fatty acid. This enzyme has been named ganglioside ceramidase.

Features of culture of the above N285 strain belonging to genus Nocardia in the various culture media according to visual observation and microscope observation are as follows:

A. Microscopical Observation

Short hyphae of 5 –10 μm formed by static culture in a meat extract medium, a peptone medium or a glucose-peptone-yeast extract medium. Simply branched. Straight or curved, but short rod form and readily aggregated in case of liquid shaking culture.

B. State of Growth on the Media (1) Sucruose-Nitrate Agar Medium

Growth good.

White peach color colonies formed in the form of convex circle or circle. Hyphae short.

(2) Glucose-Asparagine Agar Medium

Growth somewhat good.

White brown colonies formed in amorphous with periphery edge.

(3) Starch Agar Medium

Growth somewhat good.

White brown colonies formed in large circle.

(4) Tyrosine Agar Medium

Growth somewhat good.

White brown colonies formed in amorphous, glanules with convex circle.

Hyphae long.

(5) Yeast-Malt Agar Medium

Growth somewhat good.

Milky white colonies formed in somewhat large convex circle.

In these media (1)-(5), no production of pigment at the back of hyphae.

C. Physiological Properties

Aerobic, non-motile.

Growing temperature range: 15°-30° C.

Liquefaction of gelatin: Negative.

Hydrolysis of starch: Negative.

Production of melanine-like pigment (tyrosine agar medium): Negative.

Nitrate reduction ability: Positive.

Denitrification reaction: Negative.

MR test, VP test, production of indole: Negative.

Utilization of inorganic nitrogen source:

Possible (Growth is possible in all media other than those of succinic acid or glutamic acid).

Production of acid from sugar: Negative with glucose, galactose, mannose and sucrose.

Catalase: Positive.

Assimilation of carbon source: (on Pridham and Gottlieb agar medium)

(1) L-arabinose: —
(2) D-xylose: —
(3) D-glucose: +
(4) D-fructose: +
(5) Sucrose: +
(6) L-rhamnose: —
(7) Raffinose: —
(8) Mannitol: —

This strain N285 was identified as a strain belonging to genus Nocardia from the feature such as form of colonies and simple branch of hyphae and was named Nocardia sp. N285. The strain has been deposited at Fermentation Research Institute, Agency of Industrial Science and Technology, bearing FERM P-9540 and transferred to deposition under the Budapest Treaty as FERM BP-1830.

SUMMARY OF THE INVENTION

This invention is based on the above facts and provides a novel ganglioside ceramidase having the following physico-chemical properties:

Substrate specificity: It has substrate specificity at least for GD1a, GM1, GM2 and GM3.

Enzyme action: It acts at least on GD1a, GM1, GM2 and GM3 and catalyzes the reaction of hydrolysis of ganglioside to lysoganglioside and fatty acid. This invention further provides a process for preparation of a novel ganglioside ceramidase, characterized by culturing ganglioside ceramidase producing microorganism belonging to genus Nocardia in a culture medium and isolating ganglioside ceramidase from the culture.

DESCRIPTION OF THE INVENTION

Figure 1:
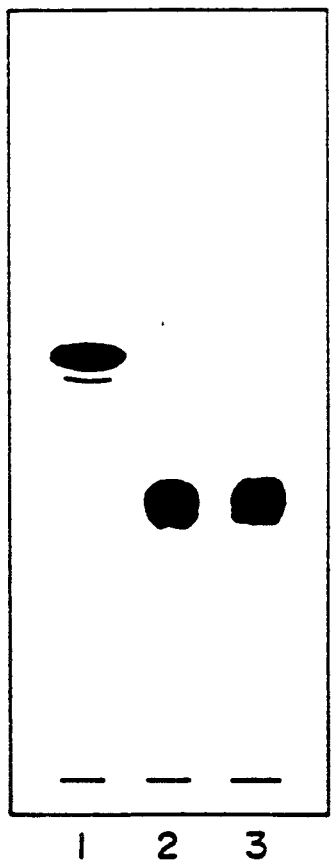
FIG. 1 shows results of HPTLC assay for decomposition product obtained by allowing ganglioside ceramidase to act on GM2 as a substrate.
Figure 1:
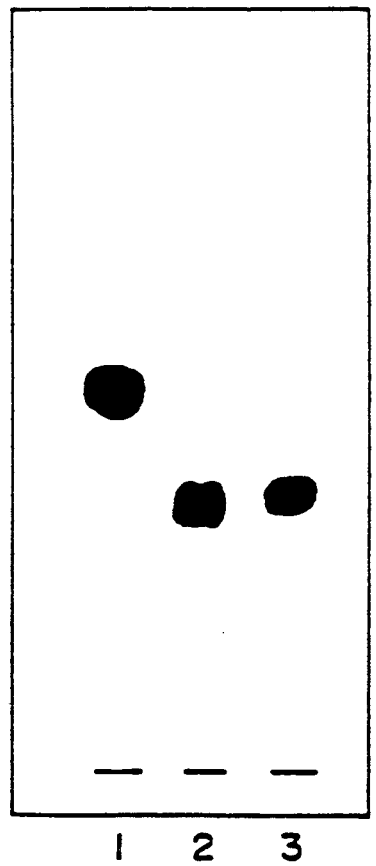

First the ganglioside ceramidase of this invention may be one having at least the physicochemical properties of the following substrate specificity and enzyme action:

(1) Substrate specificity: It has substrate specificity at least for GD1a, GM1, GM2 and GM3, (2) Enzyme action: It acts at least on GD1a, GM1, GM2 and GM3 and catalyzes the reaction of hydrolysis of ganglioside to lysoganglioside and fatty acid.

As the ganglioside ceramidase producing microorganisms in this invention, the above mentioned strain N285 belonging to genus Nocardia can be exemplified, but this is merely one example and all of other ganglioside ceramidase producing microorganisms belonging to genus Nocardia can be used in this invention. Of course, microorganisms are readily mutatable naturally or artificially and futher, gene manipulation may be applied as an artificial mutating means. These mutants can also be used in this invention as far as they retain productivity of ganglioside ceramidase.

For practicing of this invention, first, ganglioside ceramidase producing microorganism belonging to genus Nocardia is cultured by the customary process for production of enzymes or antibiotics. The culturing may be of either liquid culture or solid culture.

Nutrients of culture medium may be any of those which are normally used for culture of microorganisms. Nitrogen source may be nitrogen compounds which are available such as, for example, corn steep liquor, soybean powder, peptone, various meat extracts, yeast extracts, ammonium sulfate and ammonium nitrate. Carbon source may be assimilative carbon compounds such as, for example, glucose, molasses, glycerine and sucrose. If necessary, there may also be used salts such as sodium chloride, potassium chloride, magnesium sulfate, monobasic potassium phosphate and dibasic potassium phosphate. It is preferred to add 0.01-0.5% of ganglioside such as GM1, GM2 or GM3 to culture medium to increase productivity of ganglioside ceramidase.

Culturing temperature is usually 26°-30° C. and may be optionally changed within the range where microorganisms can grow and produce ganglioside ceramidase. Culturing time varies somewhat depending on the conditions, but normally is about 50-100 hours and the culturing may be terminated at a suitable time considering the time when ganglioside ceramidase reaches maximum titer. In the thus obtained culture, ganglioside ceramidase is contained and accumulated in the microorganism.

Then, ganglioside ceramidase is extracted from the thus obtained culture to obtain a crude ganglioside ceramidase containing solution. This can be performed, for example, by the following procedure. That is, first the culture is separated into solid and liquid, the resulting wet microorganism is, if necessary, suspended in a phosphate buffer solution or tris-HCl buffer solution, then is subjected to optional combination of cell destruction treatments such as lysozyme treatment, ultrasonication and French press treatment to extract ganglioside ceramidase from the cell thereby to obtain a crude ganglioside ceramidase containing solution.

Then this crude ganglioside ceramidase containing solution is further treated by the known means for isolation and purification of protein or enzyme to obtain purified ganglioside ceramidase. For example, an aqueous protamine sulfate solution is added to the crude ganglioside ceramidase containing solution as required to remove nucleic acid, then to the solution is added an organic solvent such as acetone, methanol, ethanol or isopropanol to fractionally precipitate ganglioside ceramidase or to the solution is added ammonium sulfate or aluminum chloride, salting out ganglioside ceramidase. Thereafter ganglioside ceramidase containing fraction is precipitated from the aqueous solution and recovered.

This precipitate of ganglioside ceramidase containing fraction can be purified, for example, by electrophoresis until single spot appears. The purification procedure comprises, for example, dissolving the ganglioside ceramidase containing precipitate in a suitable buffer solution and then subjecting the solution to chromatography by an anion exchanger such as diethylaminoethyl-cellulose or diethylaminoethyl-dextran gel crosslinked type or a gel filtrating agent such as dextran gel or polyacrylamide gel. These means can be suitably combined for purification. If necessary, to the resulting purified ganglioside ceramidase is further added one or more of stabilizers such as BSA, gelatin, amino acid, sucrose, glycerin and ethylene glycol to obtain lyophilized powder of ganglioside ceramidase.

Enzyme activity of the ganglioside ceramidase of this invention is measured by the following method. Further, the ganglioside ceramidase has the following physico-chemical properties.

(1) Method of Measurement of the Enzyme Activity

Activity of ganglioside ceramidase of this invention was measured by using $^{14}C$-labelled GM2 labelled with $^{14}C$-stearic acid as a substrate. That is, 5 $\mu$g of $^{14}C$- labelled-GM2 (2.6×10⁴ cpm), 100 μg of taurodeoxycholic acid and a given amount of enzyme were made up to 100 μl with 0.2M sodium acetate buffer solution (pH 5.8). This reaction solution was shaken at 37° C. for 1-24 hours and then methanol in an amount of 5 times that of the reaction mixture was added to terminate the reaction.

The reaction solution was evaporated to dryness in the presence of nitrogen gas, then the product was extracted with chloroform/methanol (9:1) and applied on a small column (0.5 g; Iatrobeads manufactured by Iatron Co.) and further, $^{14}$C-stearic acid liberated by the enzyme reaction was eluted with 1.0 ml of the same solvent and its radioactivity was measured by liquid scintillation counter (Aloka Model 661).

One unit of the enzyme activity is defined as the amount of enzyme that hydrolyzes 1 pmol of GM2 ganglioside per hour.

$^{14}$C-labelled-GM2 labelled with $^{14}$C-stearic acid was prepared by first preparing $^{14}$C-stearic anhydride by the process described in "J. Lipid Res", 7, 174–175 (1966) and adding 5 mg of the anhydride to 2 ml of synthetic lysoganglioside GM2 (supplied by Dr. K. Sandhoff of Bonn University)-containing chloroform/methanol (2:1 v/v) to acylate it, followed by purification by TLC.

(2) Substrate Specificity 10 nmols each of glycolipids containing ganglioside as shown in Table 1 were allowed to react with 100 μl of 0.05M sodium acetate buffer solution (pH 5.8) containing 90 units of ganglioside ceramidase and 50 μg of taurodeoxycholic acid at 37° C. for 12 hours. Then, the reaction was terminated by adding 0.5 ml of methanol. The reaction mixture was evaporated to dryness in the presence of nitrogen gas and assayed by HPTLC (high performance thin layer chromatography). Decomposition rate of each glycolipid was measured with wavelength of 580 nm for ganglioside (coloring agent: resorcinol/hydrochloric acid) and with 720 nm for neutral glycolipid (coloring agent: -naphthol/sulfuric acid) by dual wavelength TLC scanner- 910 (manufactured by Shimadzu Seisakusho Co.).

The hydrolysis rate was calculated by the following formula.

Hydrolysis rate (%)=(peak area of production of lysoganglioside)×100/(peak area of remaining glycolipid+peak area of produced lysoganglioside).

The results are shown in Table 1.

TABLE 1

| | Glycolipid | Hydrolysis rate (%) |
|---|---|---|
| Neutral glycolipid | Glc-cer (note 1) | N.D. |
| | Gal-cer (note 2) | N.D. |
| | Lac-cer (note 3) | N.D. |
| | Gb3-cer (note 4) | N.D. |
| | Asialo GM1 (note 5) | N.D. |
| Ganglioside | GM 3 (note 6) | 36.2 |
| | GM 2 (note 7) | 33.3 |
| | GM 1 (note 8) | 42.2 |

TABLE 1-continued

| Glycolipid | Hydrolysis rate (%) |
|---|---|
| GD1a (note 9) | 14.4 |

Note 1: Prepared from Gaucher's spleen; Glc 1–1'cer.
Note 2: Gal 1–1'cer
Note 3: Prepared from equine red blood cells; Gal 1–4 Glc 1–1'cer.
Note 4: Prepared from porcine spleen; Gal 1–4 Gal 1–4 Glc 1–1'cer.
Note 5: Prepared from GM1 by the process described in "Biochim. Biophys. Acta" 529, 96–195 (1978); Gal 1–3 GalNAc 1–4 Gal 1–4 Glc 1–1'cer.
Note 6: Prepared by the process described in "Biochim. Biophys. Acta", 441, 488–497 (1976); NeuAc 2–3 Gal 1–4 Glc 1–1'cer.
Note 7: Prepared from Tay-Sachs brain; GalNAc 1–4 (NeuAc 2–3) Gal 1–4 Glc 1–1'cer.
Note 8: Prepared by the process described in "Biochim. Biophys. Acta", 441, 488–497 (1976); Gal 1–3 GalNAc 1–4 (NeuAc 2–3) Gal 1–4 Glc 1–1'cer.
Note 9: Prepared by the process described in "Biochim. Biophys. Acta" 441, 488–497 (1976); NeuAc 2–3 Gal 1–3 GalNAc 1–4 (NeuAc 2–3) Gal 1–4 Glc 1–1'cer.

(In the formulas, Gal means galactose; GalNAc means N-acetylgalactosamine; Glc means glucose; NeuAc means N-acetylneuraminic acid; and cer means residue of ceramide.)

From the above results, it can be seen that ganglioside ceramidase of this invention has substrate specificity at least for GD1a, GM1, GM2 and GM3.

(3) Enzyme Action

The ganglioside ceramidase of this invention acts at least on GD1a, GM1, GM2 and GM3 and catalyzes the reaction of hydrolysis of ganglioside to lysoganglioside and fatty acid.

(4) Confirmation of the Enzyme Action

Ganglioside ceramidase was allowed to act on GM2 as a substrate and the decomposition product was identified.

First, Ganglioside ceramidase was allowed to act on GM2 and the decomposition product lyso-GM2 was purified by Iatribeads column chromatography ["Biochim. Biophys. Acta", 441, 488–497 (1976)]. The purity was checked by HPTLC (Merck). The solvent systems used were chloroform/methanol/water (5:4:1) (system A) and chloroform/methanol/ammonia/water (60:40:2:8) (system B). Resorcinol/hydrochloric acid and ninhydrin reagent were used for coloration of ganglioside and lysoganglioside. α-Naphthol/sulfuric acid reagent was used for coloration of neutral glycolipid.

The results of HPTLC are shown in FIG. 1A (system A; 1 indicates GM2, 2 indicates decomposition product and 3 indicates synthetic lyso-GM2) and FIG. 1B (system B; 1 indicates GM2, 2 indicates decomposition product and 3 indicates synthetic lyso-GM2).

That is, in using the two different solvents, behavior of decomposition product of GM2 by ganglioside ceramidase on TLC was utterly the same as that of synthesized lyso-GM2.

This decomposition product showed positive reaction to ninhydrin reagent like to resorcinol/hydrochloric acid.

Neutral sugars and amino sugars in the decomposition product and the substrate GM2 were analyzed by gas chromatography after methanolysis, N-acetylation and trimethylsilylation as described in "Biochim. Biophys. Acta", 222, 339–347 (1970). Fatty acid methyl esters were analyzed by gas chromatography. The analytical conditions were as described in "Biochim. Biophys. Acta", 529, 96–195 (1978).

The results are shown in Table 2.

TABLE 2

|  |  | Decomposition product | GM2 |
|---|---|---|---|
| Sugar | Glc | 1.0 | 1.0 |
| Composition | Gal | 1.0 | 1.1 |
|  | GalNAc | 0.9 | 0.89 |
|  | NeuAc | 1.1 | 1.1 |
| Fatty acid | C16:0 | Not detected. | 1.8% |
|  | C18:0 | Not detected. | 91.8% |
|  | C20:0 | Not detected. | 6.2% |
| Base* | dC16:1 | 11.2% | 10.4% |
|  | dC18:1 | 70.2% | 69.8% |
|  | dC20:1 | 14.4% | 15.4% |

*Sphingosine base

The above results indicated that the decomposition product and GM2 contained glucose, galactose, N-acetylgalactosamine and N-acetylneuraminic acid in an equal molar concentration. Furthermore, no fatty acid was detected in the decomposition product. These results indicated that the decomposition product was a compound formed as a result of liberation of fatty acid from the substrate GM2 due to hydrolysis.

Therefore, it is clear in combination with the results of HPTLC that the decomposition product was lyso-GM2.

That the decomposition product had the structure of lyso-GM2 was also confirmed by FAB mass spectrum. The molecular ion peak (M-H)$^-$ of the substrate GM2 was detected at m/z 1382. For the decomposition product, a strong negative ion peak m/z 1116 due to lacking of fatty acid residue (mainly stearic acid) was detected. No change occurred in both its carbohydrate and sphingosine moiety.

When other ganglioside was used as substrate in place of GM2, the decomposition product was also identified to be lysoganglioside which released fatty acid.

From the above results, it was confirmed that the ganglioside ceramidase of this invention exhibits the above mentioned novel enzyme action.

The following nonlimiting examples illustrate this invention.

EXAMPLE 1

Nocardia sp. N285 (FERM P-9540, FERM BP-1830) was inoculated in 4,000 ml of heat sterilized 0.2% polypeptone liquid culture medium (pH 7.6) containing 0.1% of ganglioside GM2 and cultivated for 96 hours at 30° C. Thereafter, the culture was centrifuged to collect cells. The cells were suspended in a phosphate buffer solution (pH 7.2) and subjected to ultrasonication by Sonifier Cell Disruptor 200 (manufacture by Branson Co.) in 30 seconds interval for a total of 2 minutes. The resulting homogenate was centrifuged at 1800 G for 5 minutes to remove cell debris. The supernatant was centrifuged at 68000 G for 60 minutes and the precipitate was recovered and was added to a phosphate buffer solution (pH 7.2). The specific activity of ganglioside ceramidase of the solution was $1.7 \times 10^4$ units/mg protein.

Physico-chemical properties of the resulting ganglioside ceramidase were as follows.

(1) Substrate Specificity

It has substrate specificity at least for GD1a, GM1, GM2 and GM3.

(2) Enzyme Action

It acts at least on GD1a, GM1, GM2 and GM3 and catalyzes the reaction of hydrolysis of ganglioside to lysoganglioside and fatty acid.

(3) Optimum pH: 5.8±0.5

Method for measurement: Measurement was conducted in the same manner as in measurement of enzyme activity with changing only pH using the reaction solution referred to in the measurement of enzyme activity.

Figure 2:
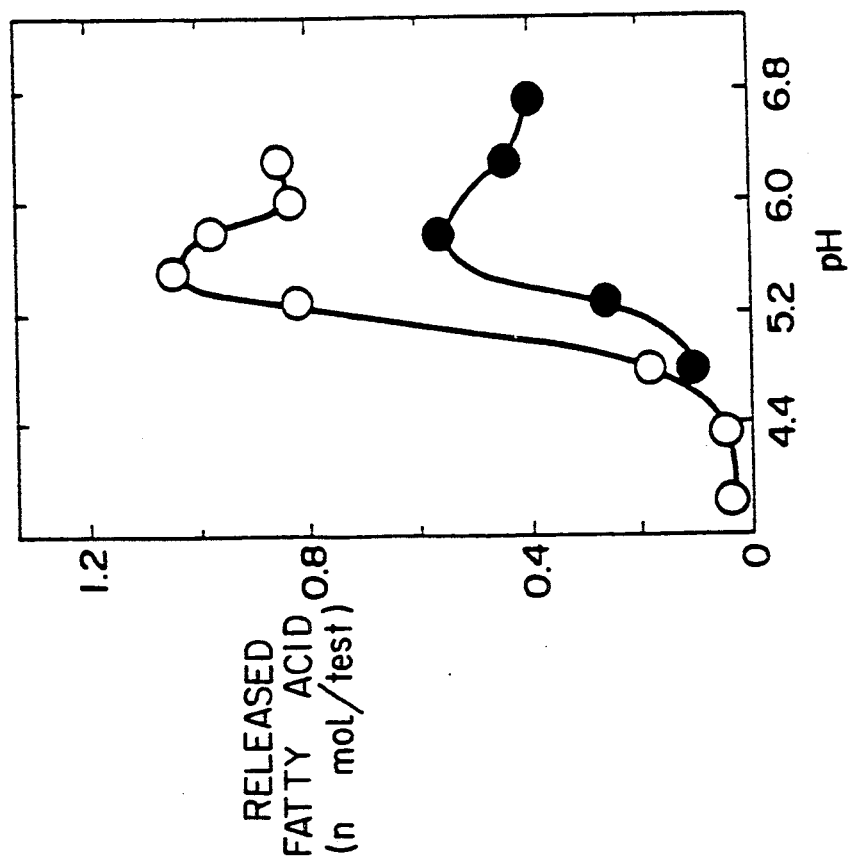
FIG. 2 shows optimum pH of ganglioside ceramidase.

The results are shown in FIG. 2, wherein O-O indicates the case of using sodium acetate buffer and ●-● indicates the case of using MES-buffer.

(4) Stable pH Range: 6–8.5

Measuring method: Enzyme was dissolved in a 10 mM MES-buffer solution and the solution was heated at 37° C. for 60 minutes and then enzyme activity was measured in accordance with the method of measurement of enzyme activity.

Figure 3:
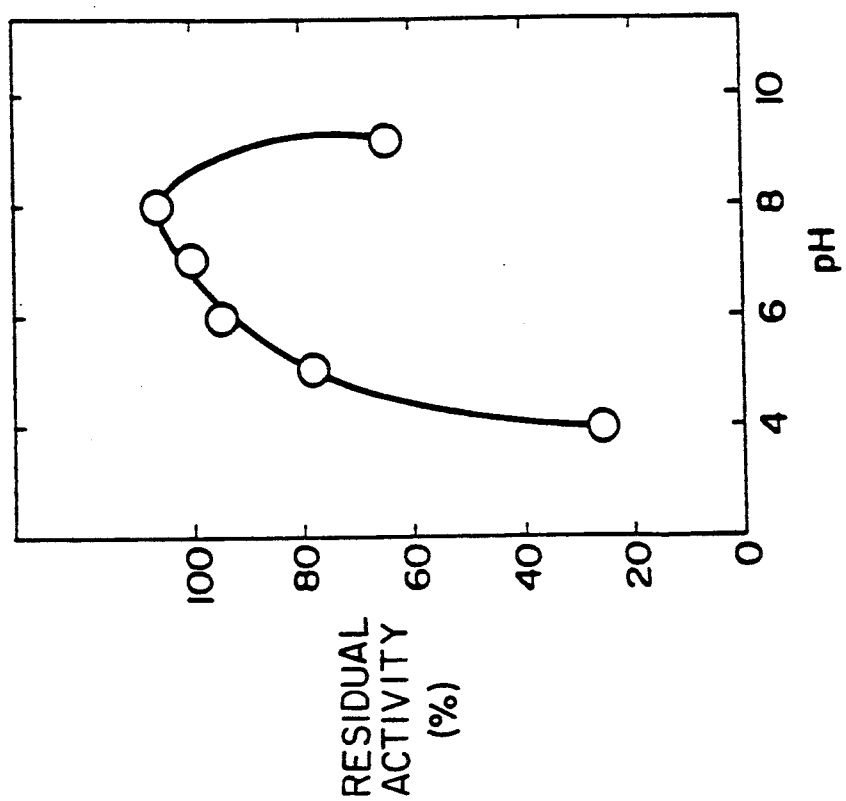
FIG. 3 shows a pH stability of ganglioside ceramidase.

The results are shown in FIG. 3, wherein O-O indicates stable pH curve in MES-buffer solution.

(5) Optimum Temperature: 35°±2° C.

Measuring method: Measurement was conducted in accordance with the method of measurement of enzyme activity with changing only reaction temperature.

Figure 4:
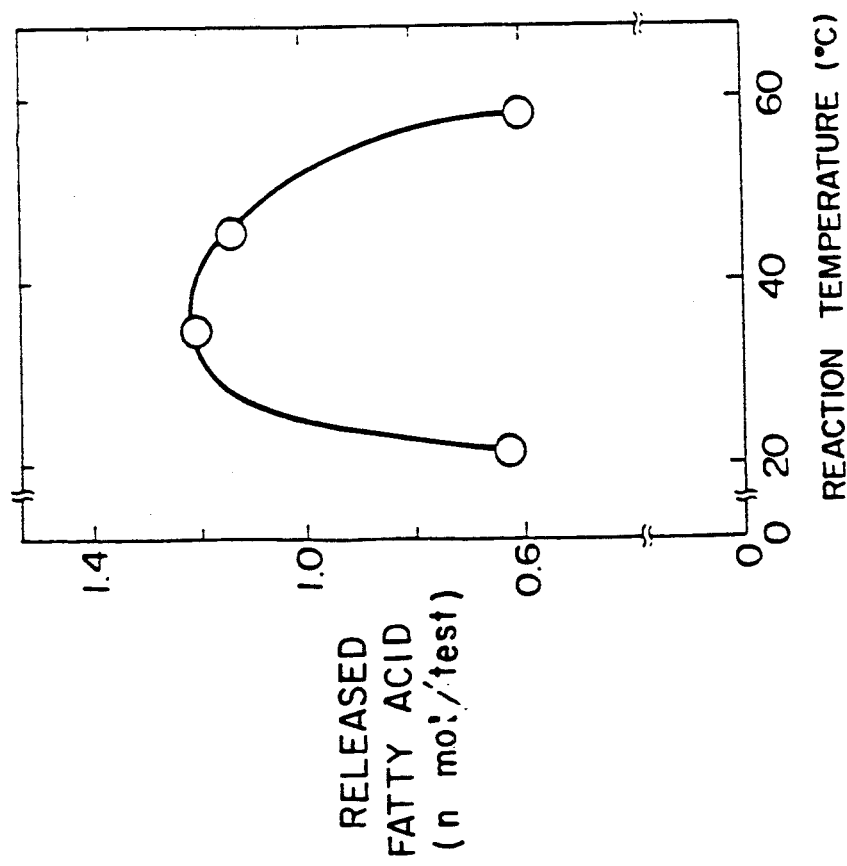
FIG. 4 shows optimum temperature of ganglioside ceramidase.

The results are shown in FIG. 4, wherein O-O indicates the results in sodium acetate buffer solution.

(6) Heat Stability

Nearly stable at 45° C. (pH 7.2, 30 minutes).

Measuring method: Enzyme was dissolved in a 10 mM phosphate buffer solution (pH 7.2) and the solution was heated at each temperature for 30 minutes and cooled with ice. Activity was measured on this enzyme solution in accordance with the method for measurement of enzyme activity.

Figure 5:
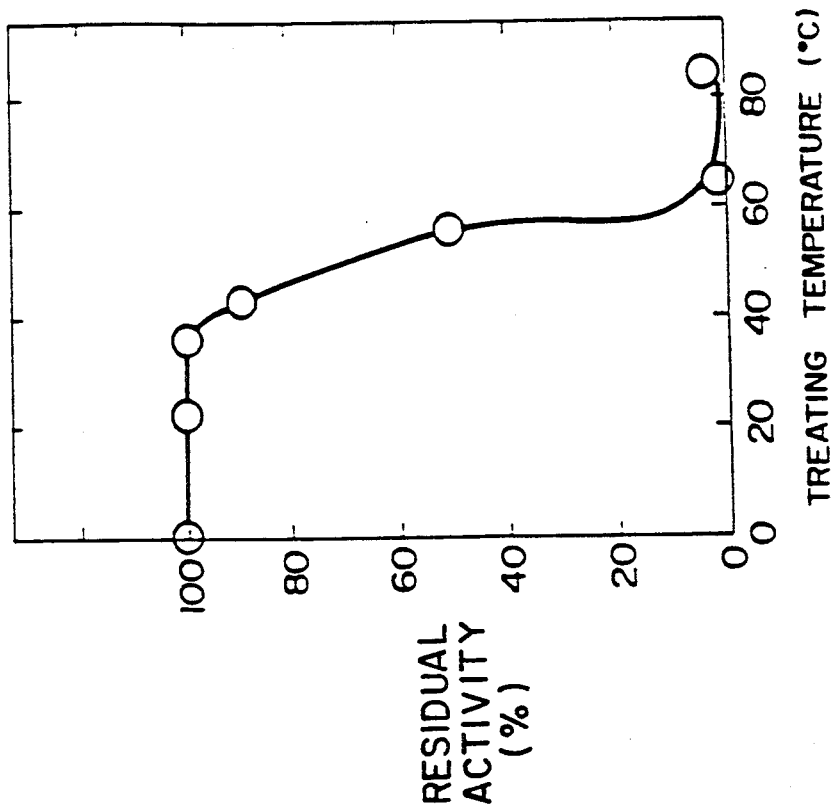
FIG. 5 shows thermal stability of ganglioside ceramidase.

The results are shown in FIG. 5, wherein O-O indicates the results in phosphate buffer solution.

(7) Inhibition and Activation with EDTA and Ions

Measuring method: To the reaction solution referred to in the measurement of enzyme activity were added EDTA and metal ions as shown in Table 3 in a concentration of 10 mM and activity was measured in accordance with the method for measurement of enzyme activity.

The results are shown in Table 3.

TABLE 3

| EDTA and ions added | Relative activity (%) |
|---|---|
| No addition | 100 |
| 10 mM EDTA | 29.9 |
| 10 mM Ba$^{++}$ | 123.6 |
| 10 mM Mg$^{++}$ | 115.3 |
| 10 mM Fe$^{++}$ | 95.1 |
| 10 mM Ca$^{++}$ | 88.2 |
| 10 mM Mn$^{++}$ | 35.4 |
| 10 mM Sn$^{++}$ | 16.0 |
| 10 mM Cu$^{++}$ | 13.2 |
| 10 mM Hg$^{++}$ | 10.4 |
| 10 mM Zn$^{++}$ | 5.6 |

This invention provides a novel enzyme ganglioside ceramidase which is useful as enzyme reagent for analysis of various gangliosides and diagnostic reagent. Further, lysoganglioside can be produced from ganglioside by the action of this ganglioside ceramidase. Moreover, from the thus produced lysoganglioside can be produced a labelled ganglioside, for example, by reintroduction of a labelled fatty acid. Furthermore, determination of amount of glycolipid can be made by dansylation with a fluorescent labelling compound dansyl chloride. In addition, fluorescence labelled ganglioside can be used as a substrate for measurement of enzyme activity of, for example, sialidase. Free amino group of lysoganglioside is linked to protein compound having carboxyl group such as albumin by customary method and the resulting product can be used as antigen or can be utilized for production of antibody. Further, it is linked to an insoluble carrier having carboxyl group and the product can be utilized as an immobilized antigen. Thus, novel diagnostic reagents are provided.

We claim:

1. A purified ganglioside ceramidase enzyme which acts on ganglioside GM2 to hydrolyze said ganglioside to a lysoganglioside and a fatty acid, where said ganglioside ceramidase essentially does not hydrolyze neutral glycolipids and essentially does not hydrolyze unglycosylated ceramides.

2. The ganglioside ceramidase of claim 1, wherein said ganglioside ceramidase further hydrolyzes at least an additional ganglioside selected from the group consisting of GD1a, GM1 and GM3 to its corresponding lysoganglioside and a fatty acid.

3. The ganglioside ceramidase according to claim 2 which has an optimum pH of $5.8 \pm 0.5$, a stable pH range of 6–8.5, an optimum temperature of $35° \pm 2°C$. and is substantially stable at 45° C. for 30 min. at pH 7.2.

4. The ganglioside ceramidase of claim 1, wherein said ganglioside ceramidase is isolated from a bacteria of the genus Nocardia.

5. The ganglioside ceramidase of claim 4, wherein said ganglioside ceramidase acts on each of GD1a, GM1 and GM3.

6. The ganglioside ceramidase of claim 1, wherein said ganglioside ceramidase is isolated from Nocardia sp. N285 (FERM BP -1830).

7. The ganglioside ceramidase of claim 6, wherein said ganglioside ceramidase acts on each of GD1a, GM1 and GM3.

* * * * *